(12) United States Patent
Perryman et al.

(10) Patent No.: US 11,745,019 B2
(45) Date of Patent: *Sep. 5, 2023

(54) SYSTEMS AND METHODS TO LOCATE AN IMPLANTABLE STIMULATOR DEVICE INSIDE A SUBJECT

(71) Applicant: Stimwave Technologies Incorporated, Pompano Beach, FL (US)

(72) Inventors: Laura Tyler Perryman, Pompano Beach, FL (US); Patrick Larson, Surfside, FL (US); Richard LeBaron, Miami Beach, FL (US)

(73) Assignee: CURONIX LLC, Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/744,952

(22) Filed: May 16, 2022

(65) Prior Publication Data

US 2022/0379125 A1 Dec. 1, 2022

Related U.S. Application Data

(63) Continuation of application No. 16/196,909, filed on Nov. 20, 2018, now Pat. No. 11,331,500.
(Continued)

(51) Int. Cl.
*A61N 1/00* (2006.01)
*A61N 1/372* (2006.01)
*A61N 1/378* (2006.01)

(52) U.S. Cl.
CPC ....... *A61N 1/37223* (2013.01); *A61N 1/3787* (2013.01); *A61N 1/37247* (2013.01)

(58) Field of Classification Search
None
See application file for complete search history.

(56) References Cited

U.S. PATENT DOCUMENTS 5,545,191 A * 8/1996 Mann ................. A61N 1/37229
607/57
6,644,321 B1 11/2003 Behm
(Continued)

FOREIGN PATENT DOCUMENTS

WO WO 2012/138782 10/2012
WO WO 2013/019757 2/2013
(Continued)

*Primary Examiner* — John R Downey
*Assistant Examiner* — Anant A Gupta
(74) *Attorney, Agent, or Firm* — Fish & Richardson P.C.

(57) ABSTRACT

Implementations provide a method that includes: placing a controller device over a surface region of the patient where the implantable wireless stimulation device has been implanted; configuring the controller device to (i) monitor a return loss representing electrical power reflected from the implantable wireless stimulation device to the controller device; (ii) compute a first path loss metric based on a first monitored return loss when the controller device is place over a first location within the surface region; (iii) compute a second path loss metric based on a second monitored return loss when the controller device is over a second location within the surface region; and (iv) generate a feedback to an operator to indicate whether the second path loss is smaller than the first path loss such that the controller device is placed at a location with more electrical energy non-inductively transferred to the implantable wireless stimulation device.

20 Claims, 14 Drawing Sheets

Related U.S. Application Data

(60) Provisional application No. 62/588,625, filed on Nov. 20, 2017.

(56) References Cited

U.S. PATENT DOCUMENTS

| | | |
|---|---|---|
| 11,331,500 B1 * | 5/2022 | Perryman .......... A61N 1/37247 |
| 2002/0042637 A1 | 4/2002 | Stover |
| 2009/0270948 A1 | 10/2009 | Nghiem et al. |
| 2010/0010565 A1 | 1/2010 | Lichtenstein et al. |
| 2012/0327804 A1 | 12/2012 | Park et al. |
| 2014/0066888 A1 | 3/2014 | Parikh et al. |
| 2014/0176063 A1 * | 6/2014 | Forsell ................. A61N 1/3787 |
| | | 320/108 |
| 2014/0275847 A1 * | 9/2014 | Perryman .............. A61B 5/369 |
| | | 607/45 |
| 2015/0257661 A1 | 9/2015 | Mestha et al. |
| 2016/0302692 A1 * | 10/2016 | Demmer .............. A61B 5/6898 |

FOREIGN PATENT DOCUMENTS

| | | |
|---|---|---|
| WO | WO 2013/025632 | 2/2013 |
| WO | WO 2013/040549 | 3/2013 |
| WO | WO 2012/103519 | 3/2014 |

\* cited by examiner

SYSTEMS AND METHODS TO LOCATE AN IMPLANTABLE STIMULATOR DEVICE INSIDE A SUBJECT

CROSS-REFERENCE TO RELATED APPLICATIONS

This application is a continuation of U.S. application Ser. No. 16/196,909, filed Nov. 20, 2018, which claims the benefit of U.S. Provisional Application No. 62/588,625, filed Nov. 20, 2017, and titled "Systems and Methods to Locate an Implantable Stimulator Device Inside a Subject." The disclosure of each of the foregoing applications is incorporated herein by reference.

TECHNICAL FIELD

This application relates generally to implantable stimulator devices.

BACKGROUND

Modulation of excitable tissue in the body by electrical stimulation has become an important type of therapy for patients with chronic disabling conditions, including pain, movement initiation and control, involuntary movements, vascular insufficiency, heart arrhythmias and various other modalities. A variety of therapeutic intra-body electrical stimulation techniques can be utilized to provide therapeutic relief for these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing.

SUMMARY

In one aspect, some implementations provide a method to locate an implantable wireless stimulation device implanted inside a patient and configured to receive electrical energy wirelessly from outside the patient via non-inductive coupling, the method including: placing a controller device over a surface region of the patient where the implantable wireless stimulation device has been implanted; configuring the controller device to non-inductively couple to the implantable wireless stimulation device such that the controller device: monitors, by modulating an impedance of a receiving non-inductive antenna on the implantable wireless stimulation device, a return loss representing electrical power reflected from the implantable wireless stimulation device to the controller device; computes a first path loss metric based on a first monitored return loss when the controller device is place over a first location within the surface region; computes a second path loss metric based on a second monitored return loss when the controller device is over a second location within the surface region; and generates a feedback to an operator to indicate whether the second path loss is smaller than the first path loss such that the controller device is placed at a location with more electrical energy non-inductively transferred to the implantable wireless stimulation device.

Implementations may include one or more of the following features.

The method may further include: configuring the controller device to monitor the return loss based on a weighted sum of multiple measurement values. The method may further include: configuring the controller device to monitor the return loss by implementing a finite impulse response (FIR) filter to reduce noise contributions from the multiple measurement values. The method may further include: configuring the controller device to monitor the return loss by removing a baseline from the weighted sum of multiple measurement values. The method may further include: configuring the controller device to monitor the return loss by removing a baseline from the weighted sum of multiple measurement values. The baseline may be removed by taking a time derivative of the multiple measured values.

The method may further include: configuring the controller device to generate a feedback by producing an audio signal to the operator indicating when more or less electrical energy is non-inductively transferred. The audio signal may be generated with increased pitch or amplitude when more electrical energy is non-inductively transferred at the second location than at the first location. The audio signal may be generated with decreased pitch or amplitude when less electrical energy is non-inductively transferred at the second location than at the first location.

The method may further include: configuring the controller device to generate a feedback by producing a visual signal to the operator indicating when more or less electrical energy is non-inductively transferred. The visual signal may be generated with increased blinking frequency or amplitude when more electrical energy is non-inductively transferred at the second location than at the first location. The visual signal may be generated with decreased blinking frequency or amplitude when less electrical energy is non-inductively transferred at the second location than at the first location.

The method may further include: configuring the controller device to generate a haptic feedback to the operator indicating when more or less electrical energy is non-inductively transferred. The haptic feedback may be generated with increased vibration frequency or amplitude when more electrical energy is non-inductively transferred at the second location than at the first location. The haptic feedback may be generated with decreased blinking frequency when less electrical energy is non-inductively transferred at the second location than at the first location.

In another aspect, some implementations provide a system including: a controller device comprising an antenna, a processor, and one or more memory storage devices; an implantable wireless stimulation device including: a non-inductive antenna configured to receive an input signal from the antenna of the controller device via radiative coupling; a circuit configured to extract electric energy from the input signal; and one or more electrodes configured to stimulate neural tissue of a subject solely using the electric energy extracted from the input signal, wherein the controller device is configured to: monitor, by modulating an impedance of the non-inductive antenna on the implantable wireless stimulation device, a return loss representing electrical power reflected from the implantable wireless stimulation device to the controller device; compute a first path loss metric based on a first monitored return loss when the controller device is place over a first location within a surface region of the subject; compute a second path loss metric based on a second monitored return loss when the controller device is over a second location within the surface region of the subject; and generate a feedback to indicate whether the second path loss is smaller than the first path loss such that the controller device is placed at a location with more electrical energy non-inductively transferred to the implantable wireless stimulation device.

Implementations may include one or more of the following features.

The controller device may be configured to monitor the return loss based on a weighted sum of multiple measured values. The controller device may be further configured to monitor the return loss by implementing a finite impulse response (FIR) filter to reduce noise contributions from the multiple measured values. The controller device may be further configured to monitor the return loss by removing a baseline from the weighted sum of multiple measured values. The controller device may be further configured to generate a feedback to indicate whether more or less electrical energy is non-inductively transferred from the controller device to the implantable wireless stimulation device.

The details of one or more implementations are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
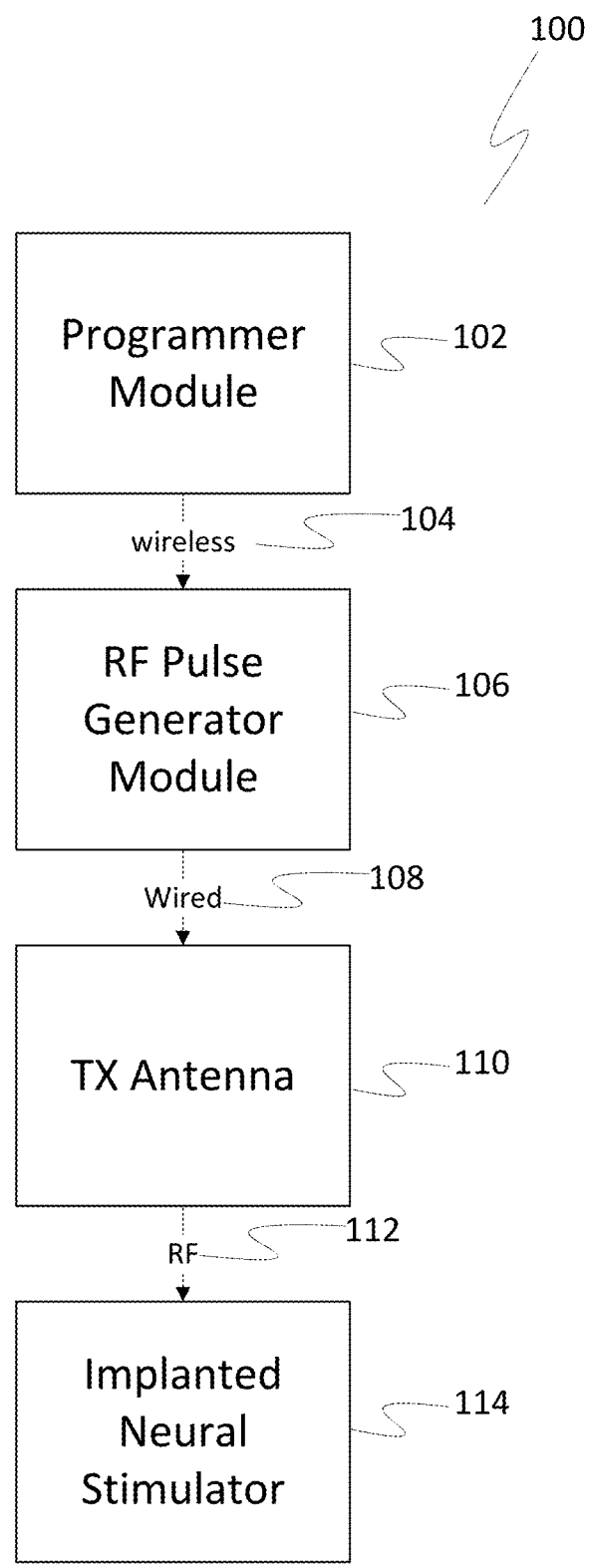
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power an implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for detecting pulse instructions, and rectification of RF electrical energy. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling, and the received RF power is used to power the implantable stimulator device. This allows such devices to produce electrical currents capable of stimulating nerve bundles without a physical connection to an implantable pulse generator (IPG) or use of an inductive coil.

In some implementations, a passive relay module may be configured as an implantable device to couple electromagnetic energy radiated from an external transmitting antenna to a wireless implantable stimulator device. In one example, the implantable device includes two monopole coupler arms connected to each other by a cable. One monopole coupler arm may be implanted in a parallel configuration with the external transmitting antenna such that linearly polarized electromagnetic waves radiated from the external transmitting antenna are received by this monopole coupler arm. Through the cable, the received electromagnetic waves may propagate to the other monopole coupler arm. In a reciprocal manner, this monopole coupler arm may radiate the received electromagnetic energy to the receiving antenna of the stimulator device. To effectively radiate the received electromagnetic energy to the receiving antenna of the stimulator device, parallel alignment of this other monopole coupler arm and the receiving antenna again may be used. In some cases, lengths of the monopole arms and length of the cable can be tailored to improve transmission efficiency, for example, at a particular operating frequency.

Some implementations utilize non-battery wireless power transfer implants, a new class of devices that can be constructed in very small form factors, enabling a minimal surgical incision and potentially unlimited product life, free of limitations and complications associated with battery powered devices. However, wireless power transfer faces various challenges. An implanted antenna is ideally very small in size to pass through a needle or cannula in order to enable a minimally invasive surgery. Generally a small antenna receives less RF power than a larger antenna, meaning the efficiency of power transfer to a very small antenna can be poor. Compounding the problem is the limited RF power that can be delivered by the external transmitting source because the Specific Absorption Rate (SAR) of RF inside the human body must to kept within safety limits. As such, optimum power transfer efficiency (or minimum path loss) must be maintained during wireless power transfer for implantable medical devices. To affect optimum power transfer, the external transmitting antenna must be aligned on the body in a favorable position relative to the implant. Estimating the location of the implant was historically only feasible using a medical imaging system, such as x-ray or ultrasound. Some implementations disclosed herein enable locating the in-situ receiver antenna, without the use of complex and expensive medical imaging techniques.

Further descriptions of exemplary wireless systems for providing neural stimulation to a patient can be found in commonly-assigned, published PCT applications PCT/US2012/23029 filed Jan. 28, 2011 and published Aug. 2, 2012, PCT/US2012/32200 filed Apr. 11, 2011 and published Oct. 11, 2012, PCT/US2012/48903, filed Jan. 28, 2011 and published Feb. 7, 2013, PCT/US2012/50633, filed Aug. 12, 2011 and published Feb. 21, 2013 and PCT/US2012/55746, filed Sep. 15, 2011 and published Mar. 21, 2013, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmitting (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrical pulses, and adjust feedback sensitivity of the RF pulse generator module 106, among other functions.

The RF pulse generator module 106 may include communication electronics that support the wireless connection 104 and the battery to power the generator electronics. In some implementations, the RF pulse generator module 106 includes the TX antenna embedded into its packaging form factor, while in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neural tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B, helical wireless implantable stimulator device 1900 shown in FIGS. 19A to 19C) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrodes. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation for maintaining effective therapy, or, in some cases, open loop control can be used.

Figure 2:
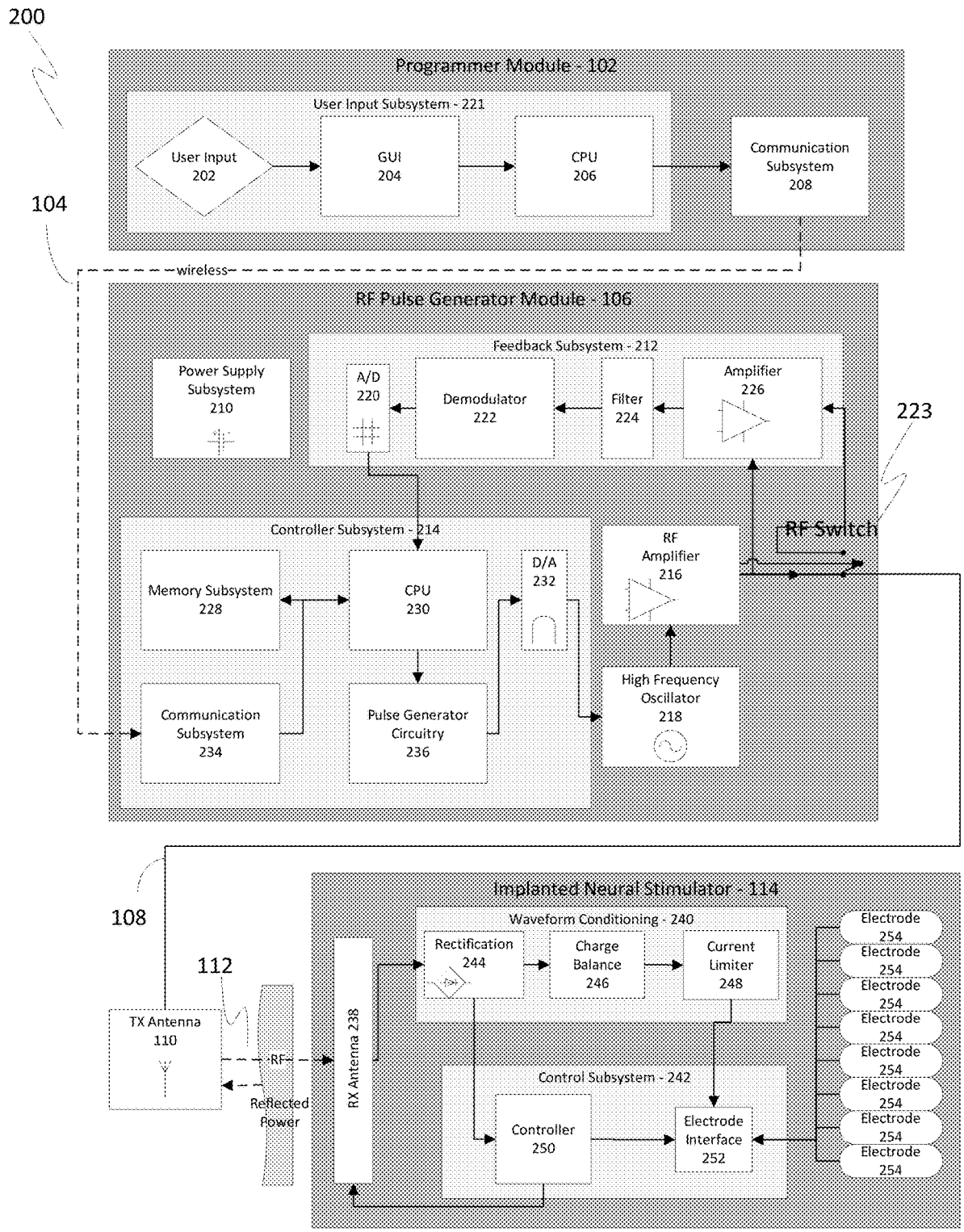
FIG. 2 depicts a more detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

| Stimulation Parameter Table 1 | |
|---|---|
| Pulse Amplitude: | 0 to 25 mA |
| Pulse Frequency: | 0 to 20000 Hz |
| Pulse Width: | 0 to 2 ms |

The RF pulse generator module 106 may be initially programmed to meet the specific parameter settings for each individual patient during the initial implantation procedure. Because medical conditions or the tissue properties can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuro-anatomy, protocols for neural modulation, and safety limits of electrical stimulation.

The controller subsystem 214 may store received parameters in the local memory subsystem 228, until the parameters are modified by new data received from the programming module 102. The CPU 206 may use the parameters stored in the local memory to control the RF pulse generator circuitry 236 to generate a pulse timing waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a digital signal may also be transmitted to the wireless stimulator device 114 to send instructions about the configuration of the wireless stimulator device 114. The digital signal is used to modulate the carrier signal that is coupled onto the implanted antenna(s) 238 and does not interfere with the input received on the same stimulator device to power the device. In one embodiment the digital signal and powering signal are combined into one signal, where the digital signal is used to modulate the RF powering signal, and thus the wireless stimulation device is powered directly by the received digital signal; separate subsystems in the wireless stimulation device harness the power contained in the signal and interpret the data content of the signal.

The RF switch 223 may be a multipurpose device such as a dual directional coupler, which passes the RF pulses to the TX antenna 110 with minimal insertion loss while simultaneously providing two low-level outputs to the feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110. The reflected RF energy and/or RF signals from the wireless stimulator device 114 are processed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can for example be used to detect fault conditions in the RF-power delivery system. In an ideal condition, when the TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can result in unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106. For example, the telemetry signal from the wireless stimulator device 114 may be coupled to its dipole antenna(s) 238, The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and can be sent via the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down-modulated using demodulator 222 and digitized through an analog to digital (A/D) converter 220. The digital telemetry signal may then be routed to a CPU 230 for interpretation. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 could alternatively generate telemetry data in real time, for example, at a rate of 8 Kbits per second. All feedback data received from the implanted stimulator device 114 can be logged against time and sampled to be stored for retrieval to a remote monitoring system accessible by the health care professional.

The RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244. The rectified signal may be fed to the controller 242 for receiving encoded instructions from the RF pulse generator module 106. The rectifier signal may also be fed to a charge balance component 246 that is configured to create one or more electrical pulses such that the one or more electrical pulses result in a charge balanced electrical stimulation waveform at the one or more electrodes. The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations. Generally, for a given electrode having several square millimeters surface area, it is the charge per phase that should be limited for safety (where the charge delivered by a stimulus phase is the integral of the current). But, in some cases, the limit can instead be placed only on the current amplitude. The current limiter 248 can automatically limit or "clip" the stimulus phase to maintain the phase within the safety limit.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can assign one or more electrodes to 1) act as a stimulating electrode, 2) act as a return electrode, or 3) be inactive. The assignment can be effectuated by virtue of RF pulse generator module 106 sending instructions to the implantable stimulator 205.

Also, in some implementations, for a given stimulus pulse, the controller 250 may control the electrode interface 252 to divide the current among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be manipulated. A given stimulus waveform may be initiated and terminated at selected times, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

In some implementations, the controller 250 can arbitrarily shape the stimulus waveform amplitude, and it may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Biphasic stimulating current pulses ensure that no net charge appears at the electrode after each stimulation cycle and the electrochemical processes are balanced to prevent net DC currents. The wireless stimulator device 114 may be configured to ensure that the resulting stimulus waveform has a net zero charge. Charge balanced stimuli are thought to have minimal damaging effects on tissue by reducing or eliminating electrochemical reaction products created at the electrode-tissue interface.

In some implementations, the charge balance component 246 uses a DC-blocking capacitor(s) placed electrically in series with the stimulating electrodes and body tissue, between the point of stimulus generation within the stimulator circuitry and the point of stimulus delivery to tissue. In a multi-electrode stimulator, one charge-balance capacitor(s) may be used for each electrode or a centralized capacitor(s) may be used within the stimulator circuitry prior to the point of electrode selection. The stimulus waveform created prior to the charge-balance capacitor, called the drive waveform, may be controlled such that its amplitude is varied during the duration of the drive pulse. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

Figure 3A:
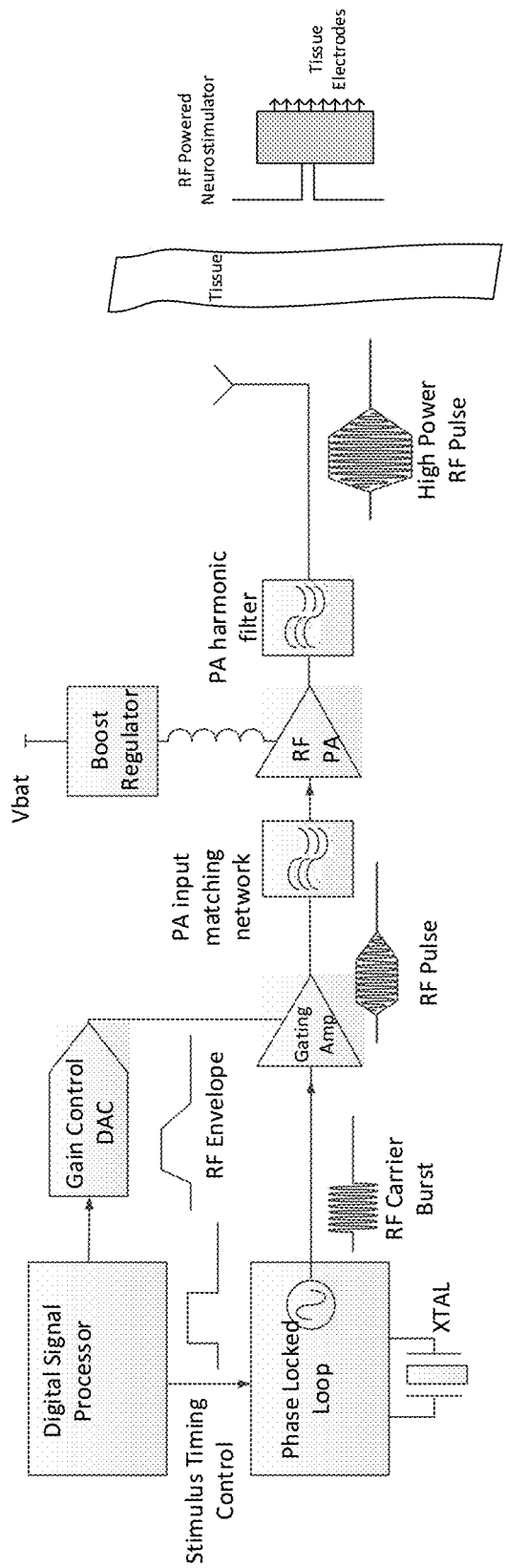
FIG. 3A is an illustration of an example of an implementation of the microwave field stimulator (MFS) transmitter for wireless power transfer to an implanted dipole antenna.
Figure 3B:
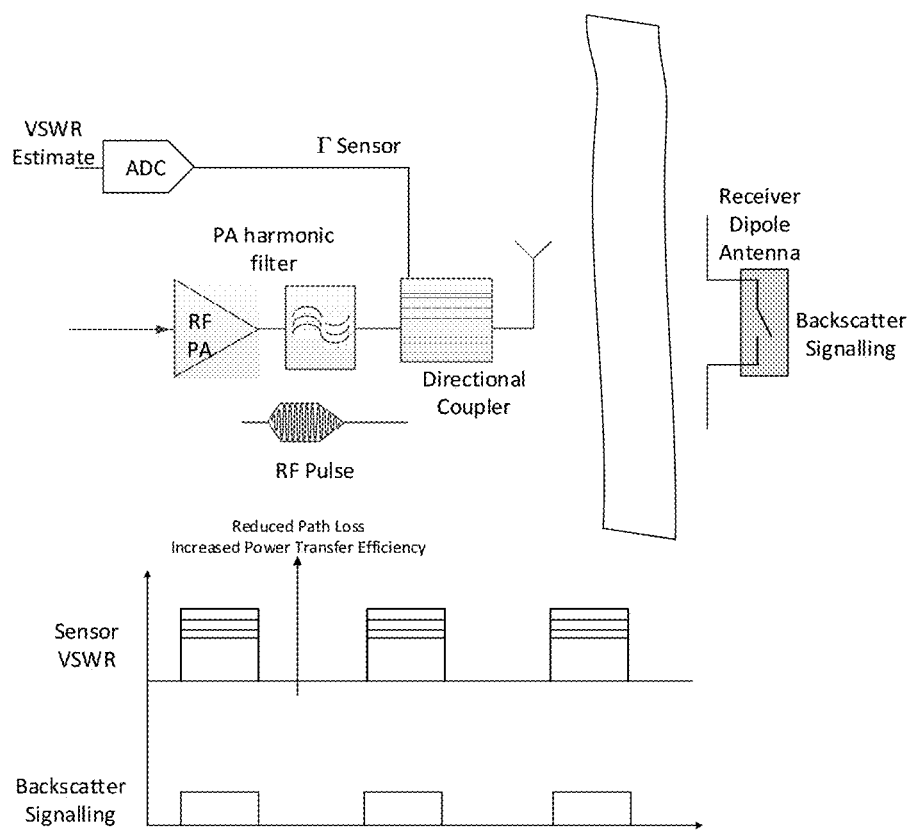
FIG. 3B is another illustration of an example of a return loss (RL) and voltage standing wave ratio (VSWR) based implant location sensor system.
Figure 3C:
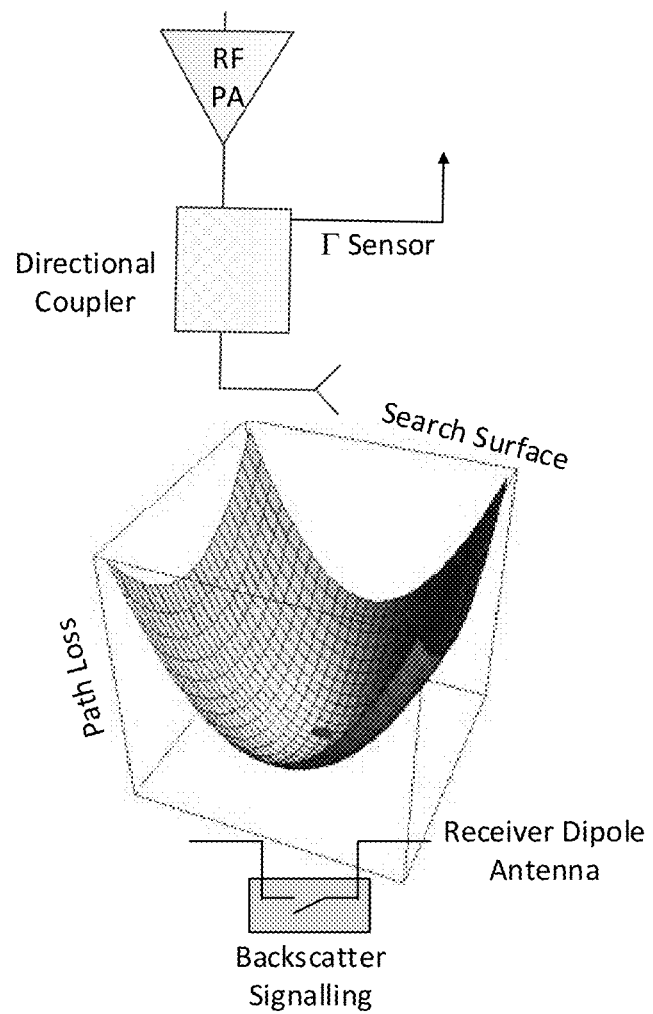
FIG. 3C is yet another illustration of an example of a 3D representation of the search surface with VSWR based implant location detection with minimum path loss.

Referring to FIGS. 3A to 3C, some implementation use the microwave field stimulator (MFS) transmitter for wireless power transfer, as illustrated in system level diagram 300. The MFS may include a digital signal processor 301, gain control 302, phase-locked loop 303, gating amplifier 304, pulse-amplitude input matching network 305, boost regulator 306, radio-frequency (RF) amplifier 307, pulse-amplitude harmonic filter 308, antenna 309, tissue boundary 310, passive neural stimulator 311, directional coupler 312, analog-digital converter (ADC) 313, and receiving dipole antenna 314. As illustrated, implanted electrodes may be used to pass pulsatile electrical currents of controllable frequency, pulse width and amplitudes. A variety of therapeutic intra-body electrical stimulation techniques may be utilized to treat conditions that are known to respond to neural modulation.

Digital signal processor 301 may generate pulse parameters such as pulse width, amplitude, and repetition rate. Digital signal processor 301 may feed pulse parameters to gain control 302, which can include a digital to analog converter (DAC). Gain control 302 may generate RF envelope 302A to gating amplifier 304. Digital signal processor 301 may feed phase-locked loop 303 with stimulus timing control 301A, which is a voltage signal that drives crystal XTAL 303A to generate RF carrier burst 303B. RF carrier burst 303B arrives at gating amplifier to modulate RF envelope 302A such that RF pulse 304A is generated to feed pulse-amplitude input matching network 305.

Output from pulse-amplitude input matching network 305 is provided to RF amplifier 307 under a bias voltage from boost regulator 306. Subsequently, a harmonic filter 308 mitigates harmonic distortions and feeds the filtered output as a high power RF pulse to antenna 309. The high power RF pulse is transmitted from antenna 309 through skin layer 310 to reach receiver dipole antenna 314 of the implanted neural stimulator device 311 so that therapies are applied at tissue electrodes.

Some implementations incorporate location detection of the implanted neural stimulator device 311 via Γ Sensor subsystem of FIG. 3B. The Γ Sensor ("gamma" sensor or "reflection" sensor) is used to measure the voltage standing wave ratio (VSWR), from which the return loss (RL) is computed. The return loss of the RF signal can be exploited to detect a backscatter signal 316 that is modulated by the implanted stimulator device 311. The backscatter signal 316 is received at antenna 309 and routed via directional coupler 312 to analog-digital converter (ADC) 313 so that an estimate of VSWR 317 may be obtained.

The location detection method can be used to determine the most advantageous position for the transmitting antenna 309, thereby minimizing the path loss from the transmitter antenna 309 to the receiver antenna 314. The operation of searching for the stimulator device 311 is premised on the stimulator device 311 modulating the impedance of its receiving antenna 314. This modulation is detectable by the Γ Sensor of FIG. 3B, where F is the reflection coefficient (or return loss) of the transmitter antenna 309. When the stimulator device 311 is configured to operate in location mode, the impedance of receiver antenna 314 is periodically modified by a switched load 316. When the load 316 is changed, the impedance of the receiver antenna 314 is altered such that the receiver antenna 314 reflects RF energy. Subsequently, the transmitter antenna 309 also experiences an impedance change, which is detected by the Γ Sensor of FIG. 3B. The measurements at the Γ Sensor represent the forward and reverse RF power levels, from which Γ is computed. As load 316 at the receiver antenna 314 is actively modulated by the stimulator device 311, the shift of the signal seen by the Γ Sensor has an observed magnitude. The magnitude of the shift also depends on the coupling of the two antennas. As the transmitter antenna 309 is brought closer to the receiver antenna 314, the RF coupling improves, and the magnitude of signal from the Γ Sensor increases.

When the system is engaged in location mode, the controller 250 monitors the reflection coefficient (Γ) and computes the associated Voltage Standing Wave Ratio (VSWR) according to the following equation:

$$VSWR = \frac{1+|\Gamma|}{1-|\Gamma|}$$

The path loss decreases (the power transmission improves) as the transmitter antenna 309 is moved into better alignment with the implanted receiver antenna 314. As illustrated by the concave 3-D surface showing the path loss versus antenna alignment in FIG. 3C, the optimal location of the transmitter antenna 309 corresponds to the minimum value of the path-loss surface. Finding the low point on the path-loss surface is the goal of the user while moving the transmitter antenna 309 across the surface of subject's body. While operating in this mode, the MFS 300 could give audio and/or visual and/or haptic feedback to the user indicating when the transmitter antenna 309 is approaching the optimal alignment. By the use of this implant location method, the path loss for the RF power can be substantially minimized, meaning the MFS 300 can provide the most efficient power delivery to the stimulator device 311.

In some implementations, the implant-location algorithm employs a finite impulse response (FIR) filter for reducing noise from the Γ Sensor. By computing the summation (SUM) of Γ values from the most recent N pulses, then removing the baseline offset by taking the time derivative of the smoothed data, the backscatter transitions or "steps" of Γ can be extracted from a noisy signal. In this application, it may be advantageous to resolve small steps of Γ because the influence of the receiver antenna 314 upon the value of Γ (measured at the transmitter antenna 309) can be very small relative to the noise.

The backscatter transitions in the time derivative of Γ can be enhanced by raising the result to an M-th power, where M is positive and even, such that any derivative value less than 1.0 can be reduced to approximate zero, while any value above 1.0 can be enhanced. An example of a computationally efficient algorithm to perform the described signal conditioning is as follows:

Let N be an integer greater than 1, where N is the number of points or "taps" of the FIR filter. Then calculate the sums: Sum0, Sum1, Sum2, . . . , Sum5 and corresponding time derivatives, Delta0, Delta1, Delta2, . . . , Delta5 of the received signal which in this example is the unprocessed reverse voltage values (REV(n)) as sampled at the MFS reverse voltage detector.
u1=Sum0
Sum0=REV(n)
u2=Sum0
Delta0=u2−u1
u1=Sum1
Sum1=(Sum1+Sum0−Sum1/N)
u2=Sum1
Delta1=u2−u1
u1=Sum2
Sum2=(Sum2+Sum1/N−Sum2/N)
u2=Sum2
Delta2=u2−u1
u1=Sum3
Sum3=(Sum3+Sum2/N−Sum3/N)
u2=Sum3
Delta3=u2−u1
u1=Sum4
Sum4=(Sum4+Sum3/N−Sum4/N)
u2=Sum4
Delta4=u2−u1
u1=Sum5
Sum5=(Sum5+Sum4/N−Sum5/N)
u2=Sum5
Delta5=u2−u1

When calculating successive sums, a divide-by-N operation may be added in order to avoid generation of very large numbers in the computations. The number of data sample points averaged, N, can be chosen strategically to remove random noise and/or known periodic noise signals. However, N must be chosen strategically such that the algorithm has suitable settling time for the given application, and the filtering does not obscure the desired signal. For example, when looking for backscatter signals, N should be less than or equal to the number of samples per backscatter period. Otherwise the backscatter signal itself can be filtered and lost. In the following examples, N=8, and RF pulse rate=3 kHz.

Figure 4A:
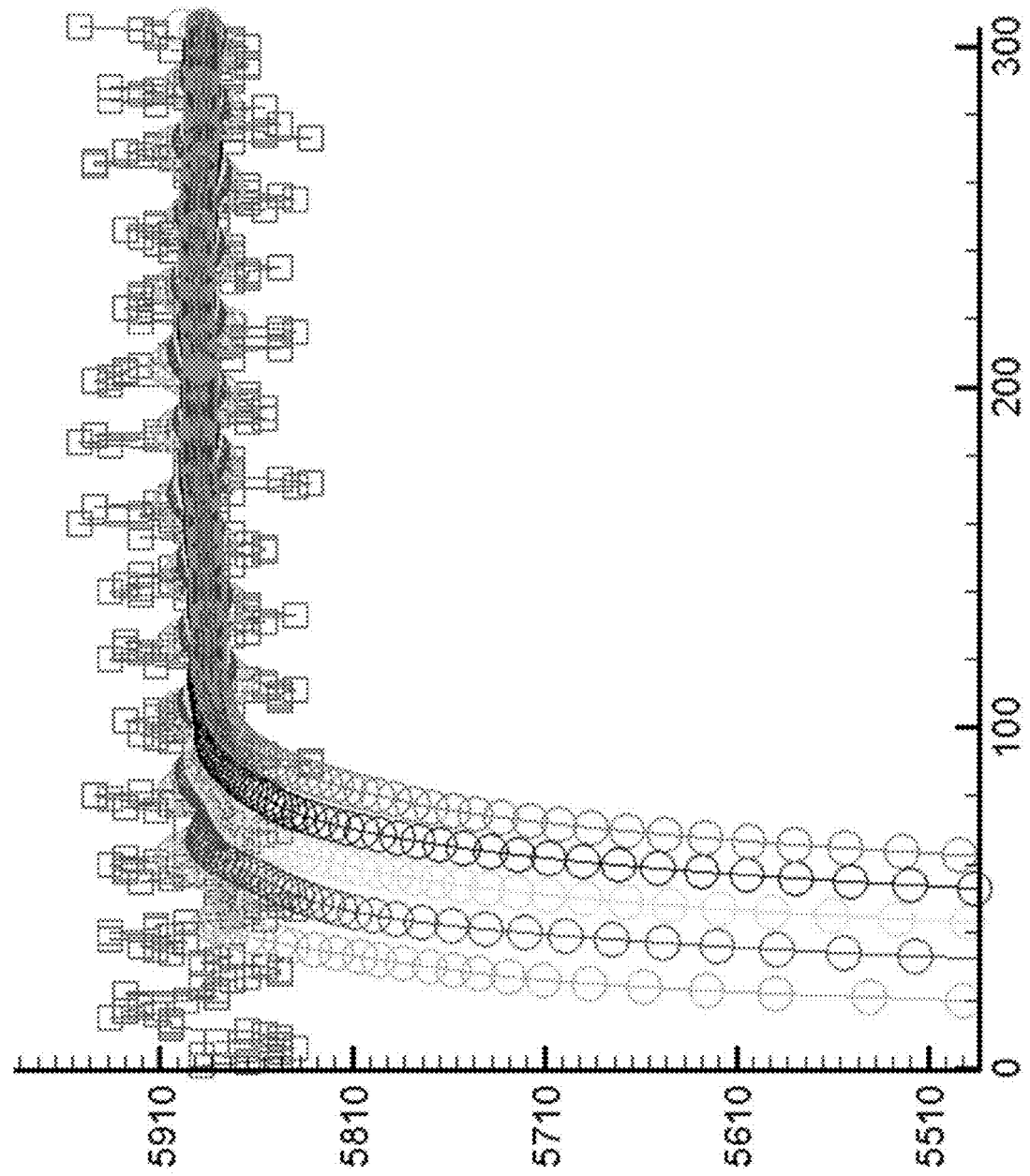
FIG. 4A-4I show various examples from simulation computations for RL and VSWR-based implant location detection.
Figure 4B:
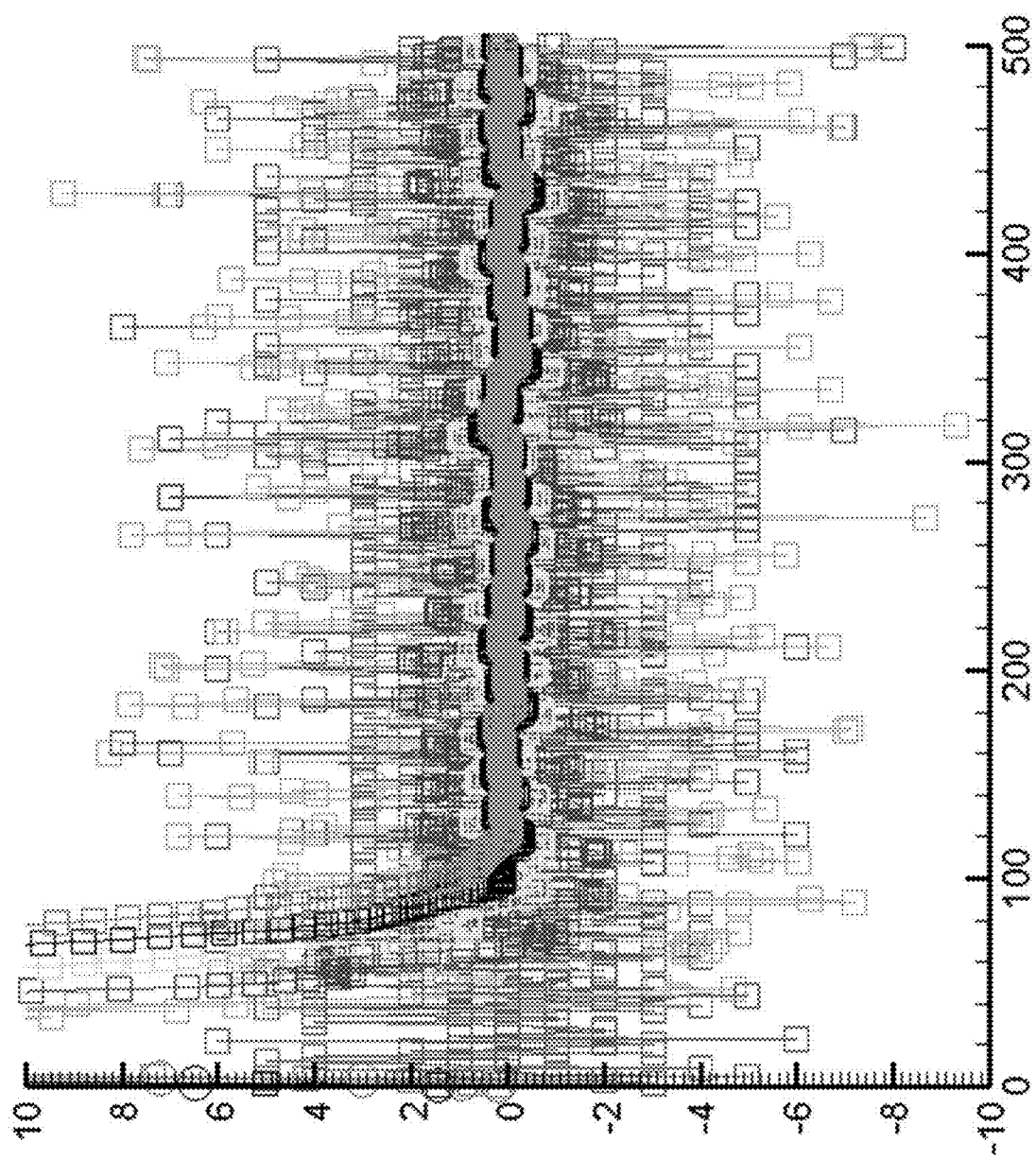
Figure 4C:
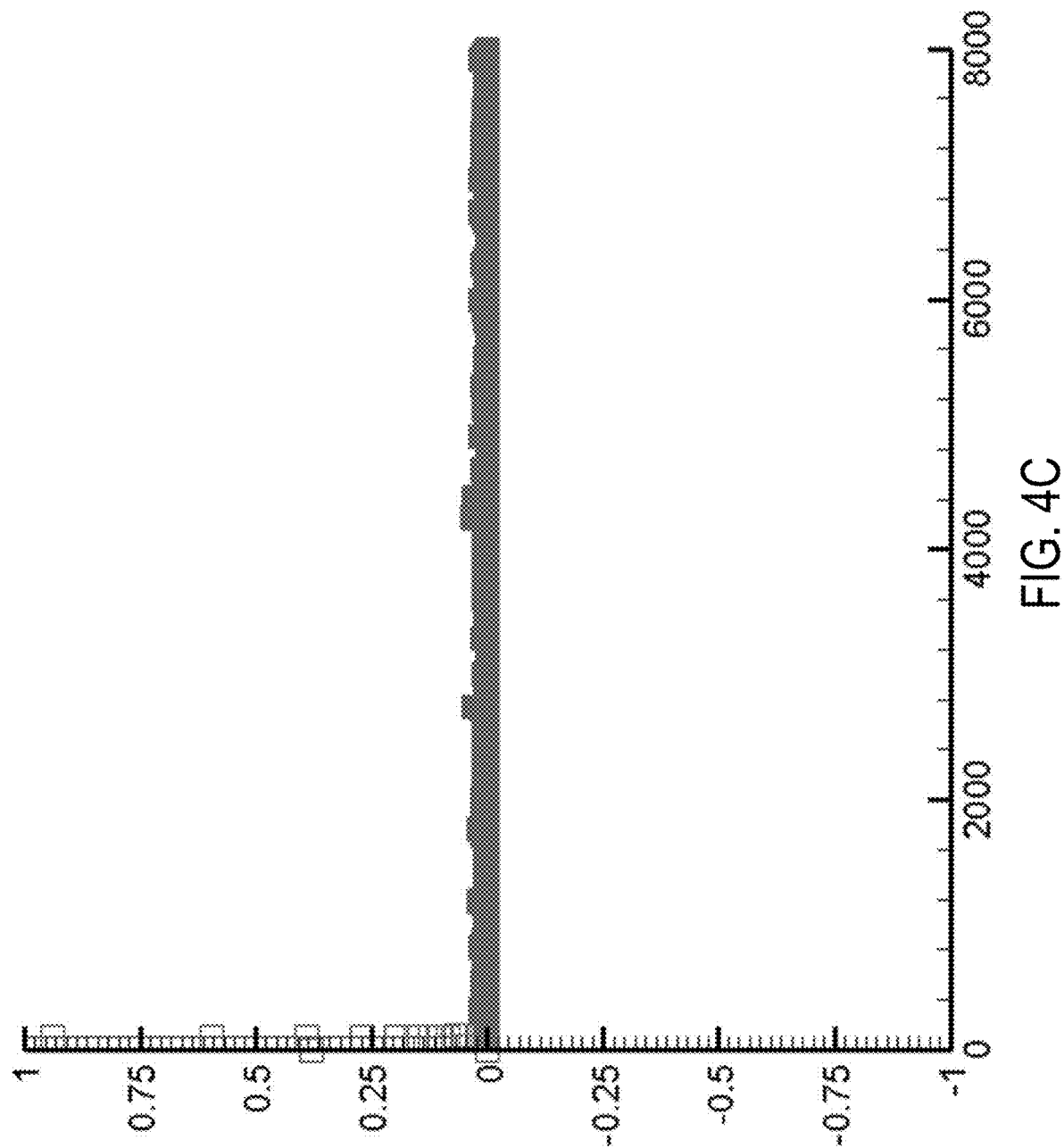

Shown in FIG. 4A is an example of the algorithm results plotted versus sample count (horizontal axis), calculated as Sum0 through Sum5. In this display, Sum0 results are represented by red squares, Sum1 results are represented by green circles, Sum2 results are represented by dark blue circles, Sum3 results are represented by light blue circles, Sum4 results are represented by black circles, and Sum5 results are represented by magenta circles. FIG. 4B shows the respective time derivatives versus sample count (horizontal axis), for Delta0 through Delta5. In this display, Delta0 results are represented by red squares, Delta1 results are represented by green squares, Delta2 results are represented by dark blue squares, Delta3 results are represented by light blue squares, Delta4 results are represented by black squares, and Delta5 results are represented by magenta squares. The results show an increase in the settling time as the number of sums is increased. Sum0 results (red squares), for example, has noise with an undesired periodic beat. In one instance, letting N=8 (eight points averaged) may filter out the beat sufficiently while minimizing settling lag. By the $5^{th}$ sum (magenta circles), the noise in the results is substantially smoothed out. If derivatives are subsequently taken and raised to an even power, the result will be a positive value. The derivatives smaller than 1.0 can be reduced, while any derivatives larger than 1.0 can be enhanced. The derivative of the $5^{th}$ pass, raised to the $4^{th}$ power, (Delta5)^4, versus sample count (horizontal axis) is shown in FIG. 4C. In this case the backscatter signal was turned off and only environmental noise was present. With this algorithm, the unwanted noise was substantially filtered out, as shown in FIG. 4C.

Figure 4D:
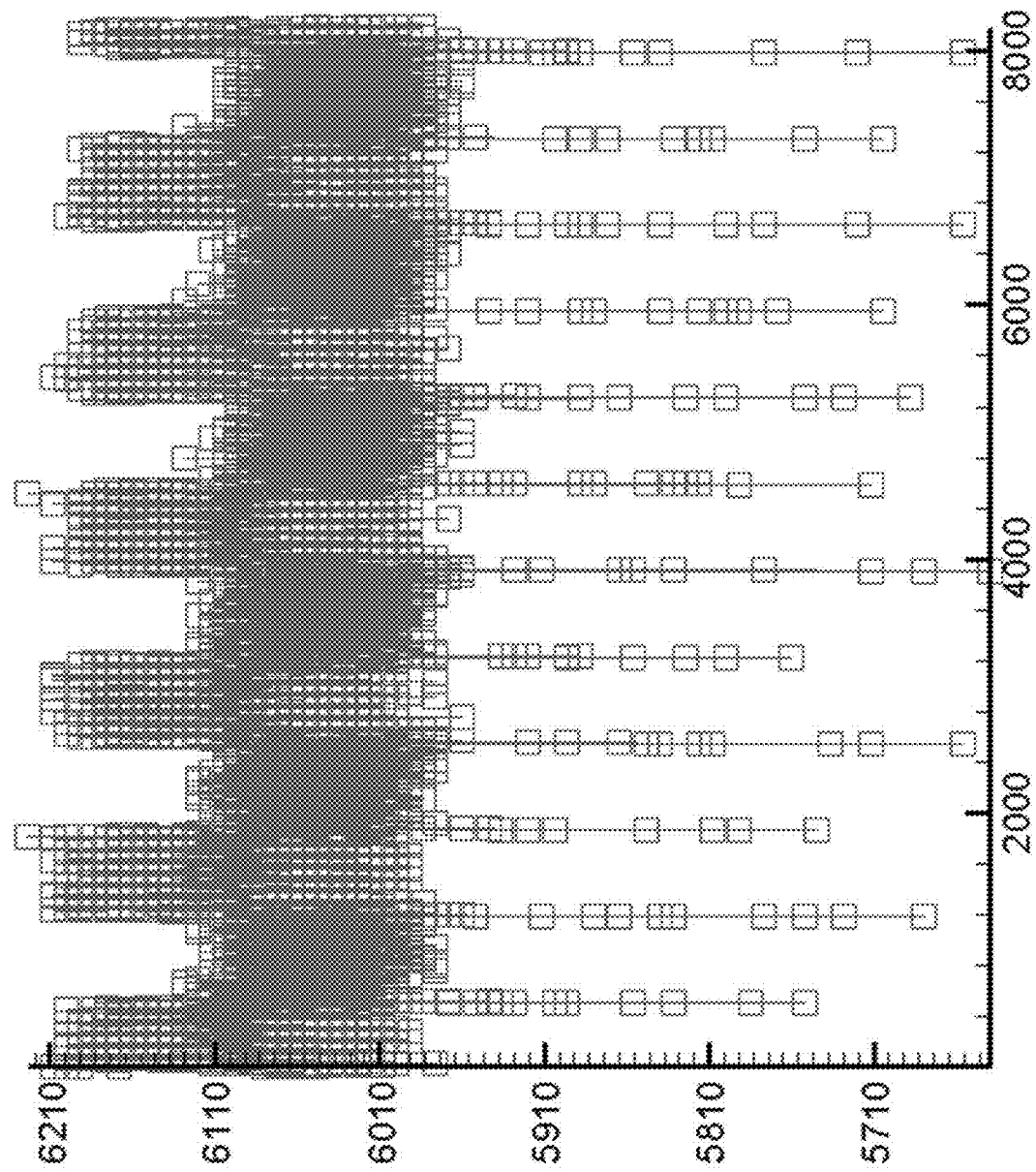
Figure 4E:
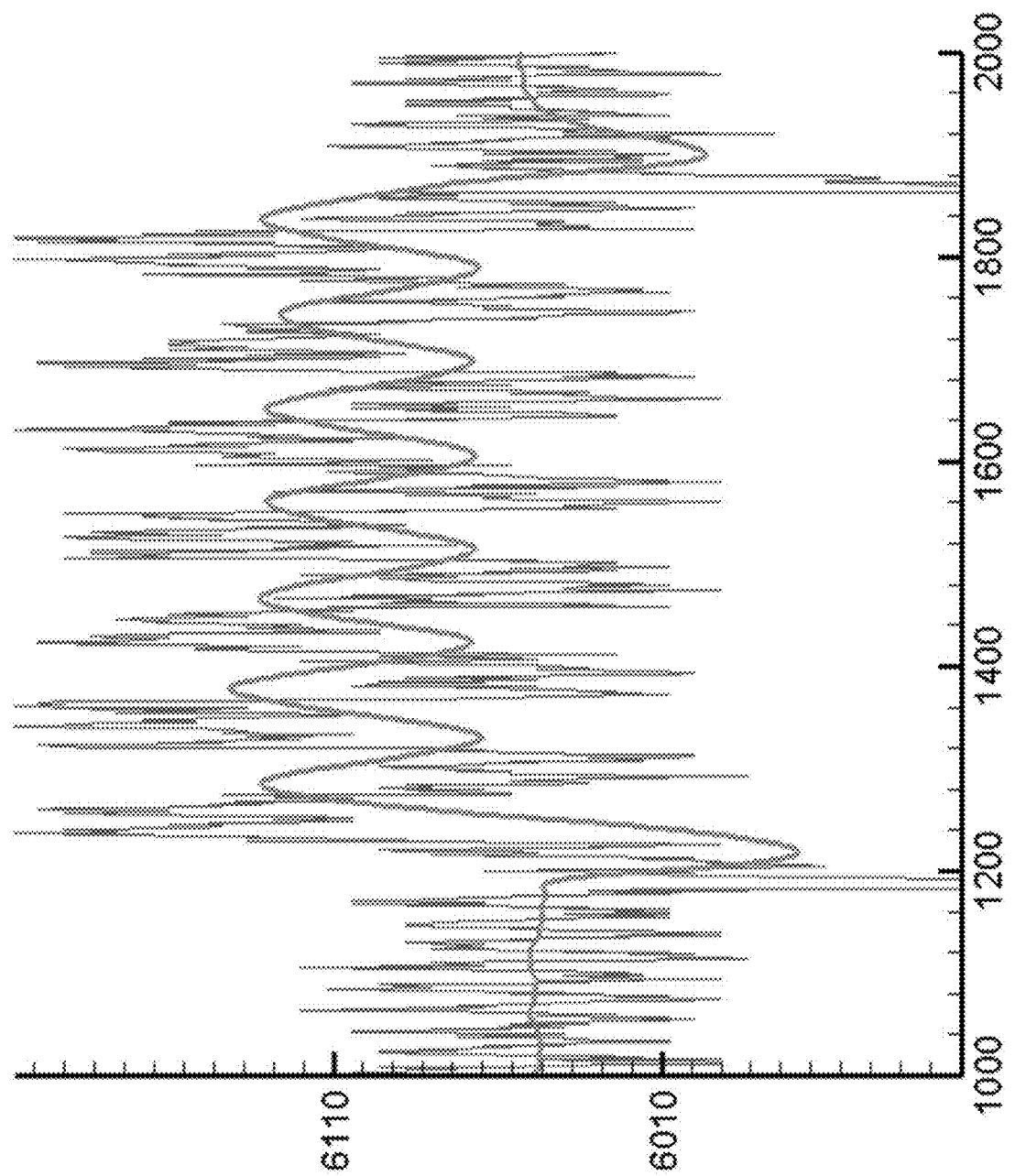
Figure 4F:
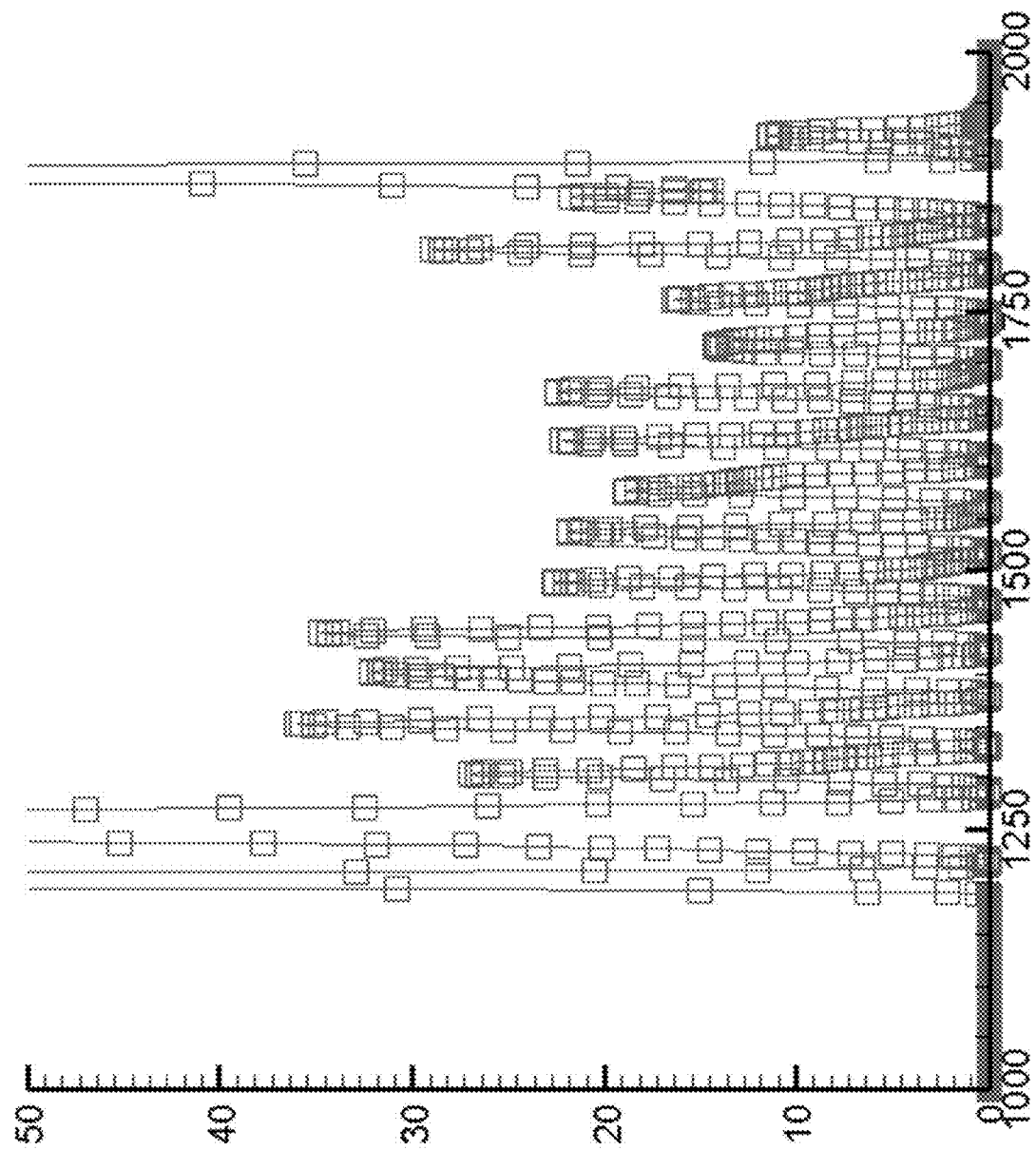
Figure 4G:
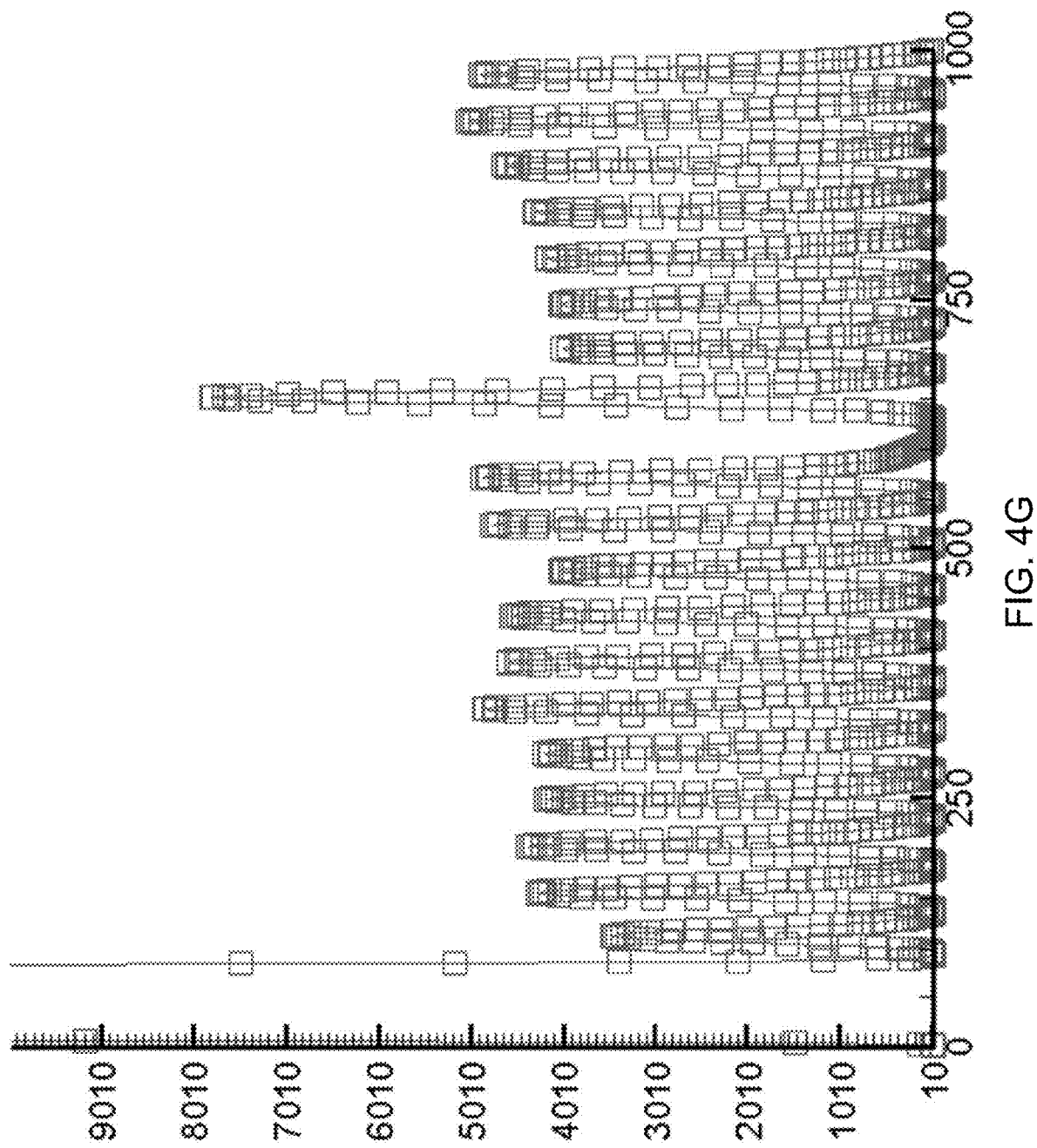
Figure 4H:
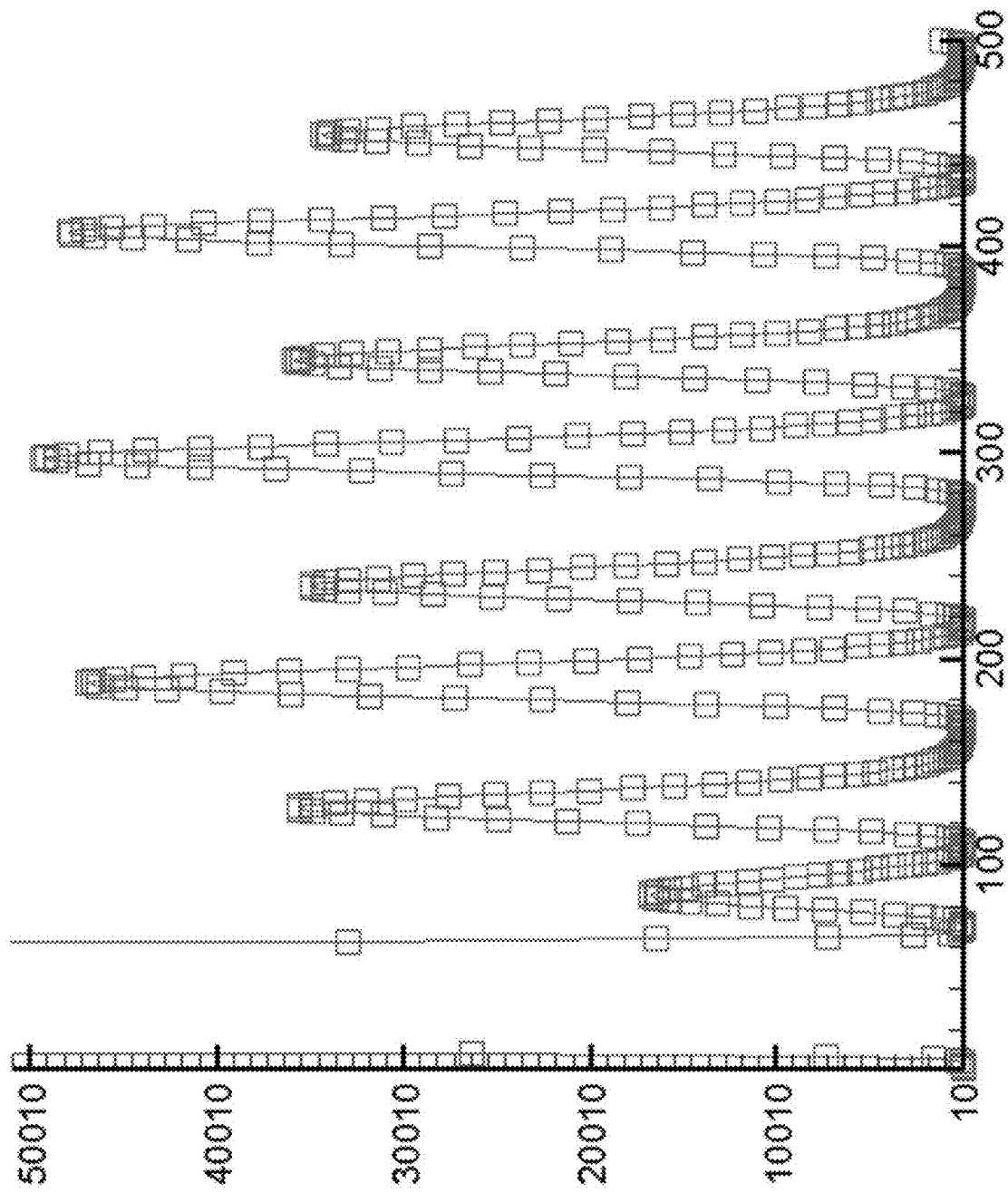
Figure 4I:
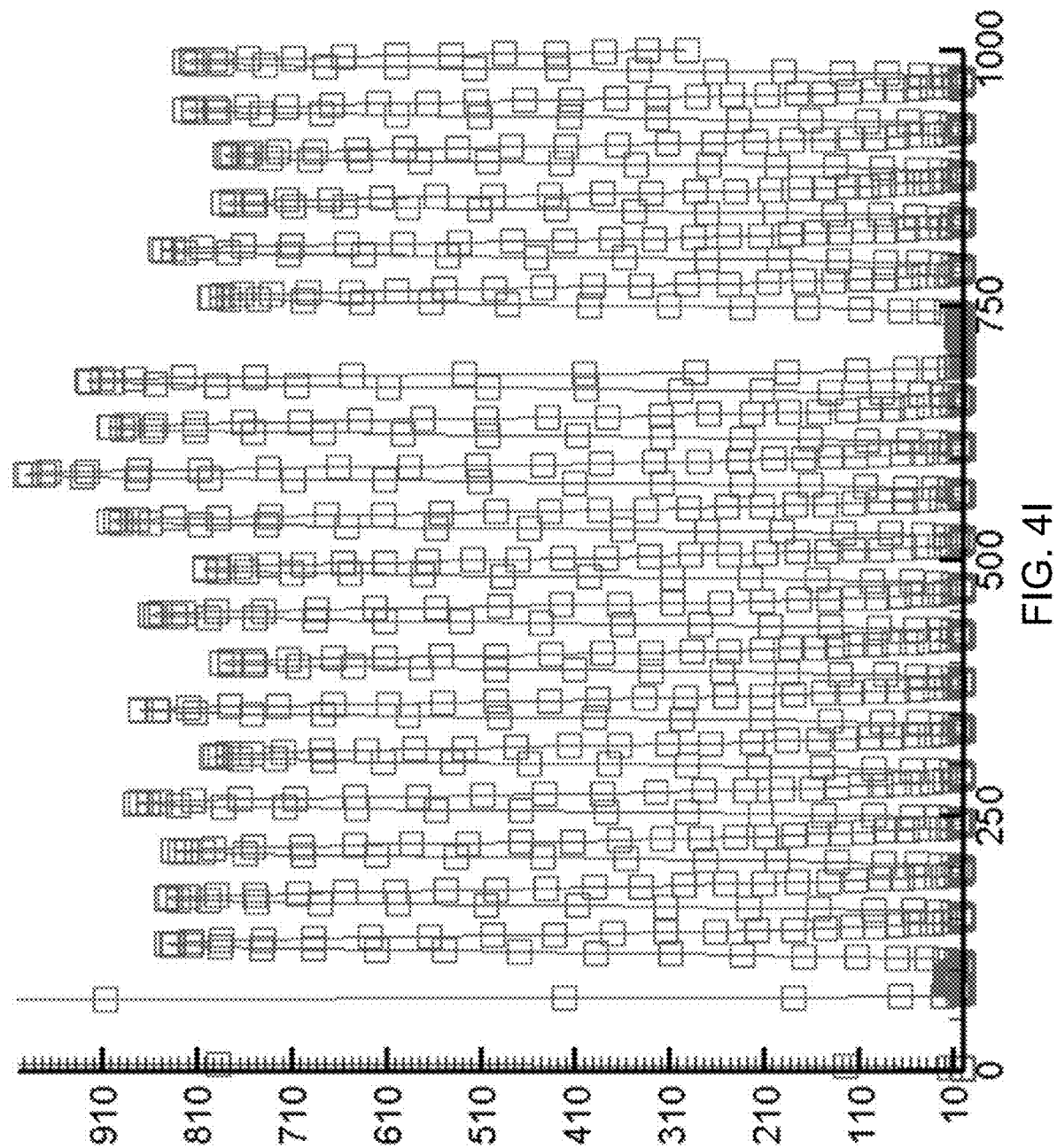

FIG. 4D shows a backscatter signal 316 for an implanted stimulator device 311 that is far from the transmitter antenna 309, and the change in Γ is near the limit of detection. In FIG. 4E the same result is shown on a smaller time scale to show the signal in detail. From sample count 1,000 to 1,200, the backscatter signal 316 was turned off, then it was enabled from 1,200 to about 1,800, then it was off again to sample count 2,000. The red trace is results from Sum0 which is the backscatter signal 316 superimposed on the noise. The magenta trace shows results from Sum5, which is flat when the backscatter signal 316 is off and is sinusoidal when the backscatter signal 316 is on. The derivative of results from Sum5, raised to the $4^{th}$ power, (Delta5)^4, enhances the signal as shown in FIG. 4F, which demonstrates a weak backscatter signal can be detected in a noisy environment. In contrast, a strong backscatter signal 316 with the same filtering algorithm is shown FIG. 4G. A stronger signal such as that of FIG. 4G may occur when the path loss from the transmitter antenna 309 to the receiver antenna 314 is minimized. Two additional examples of detection of backscatter signal 316 are shown in FIGS. 4H and 4I. These signals are considered to be difficult to resolve because the scattering intervals may be randomly timed. FIG. 4H shows the case when two implanted stimulator devices 311 are backscattering simultaneously, and FIG. 4H shows the case when an implanted stimulator device 311 generates chaotic backscattering.

A number of implementations have been described. Nevertheless, it will be understood that various modifications may be made. Accordingly, other implementations are within the scope of the following claims.

What is claimed is:

1. A method to locate an implantable wireless stimulation device implanted inside a patient and configured to receive electrical energy wirelessly from outside the patient via non-inductive coupling, the method comprising:
    placing a controller device over a surface region of the patient where the implantable wireless stimulation device has been implanted;
    configuring the controller device to non-inductively couple to the implantable wireless stimulation device such that the controller device:
        monitors, by modulating an impedance of a receiving non-inductive antenna in the implantable wireless stimulation device, a return loss representing electrical power reflected from the implantable wireless stimulation device to the controller device;
        computes a first path loss metric based on a first monitored return loss when the controller device is place over a first location within the surface region;
        computes a second path loss metric based on a second monitored return loss when the controller device is over a second location within the surface region; and
        generates a feedback to an operator to indicate whether the second path loss is smaller than the first path loss such that the controller device is placed at a location with more electrical energy non-inductively transferred to the implantable wireless stimulation device.

2. The method of claim 1, further comprising:
configuring the implantable wireless stimulation device in a location mode, wherein the location mode enables: (i) the impedance of the receiving non-inductive antenna to periodically change and (ii) the receiving non-inductive antenna to reflect the electrical power from the implantable wireless stimulation device to the controller device in response to the periodic changes of the impedance of the receiving non-inductive antenna.

3. The method of claim 2, further comprising:
configuring the controller device to monitor the return loss by monitoring an impedance change at a non-inductive transmitting antenna of the controller device based on the reflected electrical power from the implantable wireless stimulation device.

4. The method of claim 3, further comprising:
configuring the controller device to communicate with the implantable wireless stimulation device by transmitting the electrical power to the implantable wireless stimulation device using the non-inductive transmitting antenna.

5. The method of claim 4, further comprising:
configuring the controller device to calculate a voltage standing wave ratio based on a magnitude of a shift between the impedance change at the non-inductive transmitting antenna during (i) the transmitting of the electrical power to the implantable wireless stimulation device and (ii) the monitoring of the reflected electrical power from the implantable wireless stimulation device.

6. The method of claim 5, further comprising:
configuring the controller device to compute the first path loss metric at the first location or the second path loss metric at the second location based on the calculated voltage standing wave ratio.

7. The method of claim 5, wherein the magnitude of the shift between the impedance change at the non-inductive transmitting antenna is at least based on a coupling between the non-inductive transmitting antenna of the controller device and the non-inductive receiving antenna of the implantable wireless stimulation device.

8. The method of claim 1, wherein the second path loss being smaller than the first path loss reflects that the second location of the controller device is closer to the implantable wireless stimulation device than the first location of the controller device.

9. The method of claim 1, further comprising:
configuring the controller device to generate the feedback by producing an audio signal to the operator indicating when more or less of the electrical energy is non-inductively transferred between the controller device and the implantable wireless stimulation device.

10. The method of claim 9, wherein the audio signal is generated with increased pitch or amplitude when more of the electrical energy is non-inductively transferred at the second location than at the first location.

11. The method of claim 9, wherein the audio signal is generated with decreased pitch or amplitude when less of the electrical energy is non-inductively transferred at the first location than at the second location.

12. The method of claim 1, further comprising:
configuring the controller device to generate the feedback by producing a visual signal to the operator indicating when more or less of the electrical energy is non-inductively transferred between the controller device and the implantable wireless stimulation device.

13. The method of claim 12, wherein the visual signal is generated with increased blinking frequency or amplitude when more of the electrical energy is non-inductively transferred at the second location than at the first location.

14. The method of claim 12, wherein the visual signal is generated with decreased blinking frequency or amplitude when less of the electrical energy is non-inductively transferred at the first location than at the second location.

15. The method of claim 1, further comprising:
configuring the controller device to generate a haptic feedback to the operator indicating when more or less of the electrical energy is non-inductively transferred.

16. The method of claim 15, wherein the haptic feedback is generated with increased vibration frequency or amplitude when more of the electrical energy is non-inductively transferred at the second location than at the first location.

17. The method of claim 15, wherein the haptic feedback is generated with decreased vibration frequency or amplitude when less of the electrical energy is non-inductively transferred at the first location than at the second location.

18. The method of claim 1, further comprising:
configuring the controller device to obtain multiple instances of monitored return loss and perform a weighted sum of the multiple instances of the monitored return loss.

19. The method of claim 18, further comprising:
configuring the controller device to obtain multiple instances of monitored return loss and implement a finite impulse response (FIR) filter to reduce noise contributions from the multiple instances of the monitored return loss.

20. The method of claim 1, further comprising:
configuring the controller device to non-inductively couple to the implantable wireless stimulation device and a second implantable wireless simulation device, wherein the implantable wireless stimulation device and the second implantable wireless simulation device are both implanted in the patient.

* * * * *